United States Patent
Bizzini et al.

(10) Patent No.: US 8,679,483 B2
(45) Date of Patent: Mar. 25, 2014

(54) HIGH-YIELD METHOD FOR THE PRODUCTION OF HUMAN ANTIBODIES BLOCKING THE BIOLOGICAL ACTIVITY OF A HUMAN CYTOKINE

(75) Inventors: Bernard Bizzini, Carcassonne (FR); Helene Le Buanec, Paris (FR); Daniel Zagury, Paris (FR)

(73) Assignee: Neovacs, Paris (FR)

( * ) Notice: Subject to any disclaimer, the term of this patent is extended or adjusted under 35 U.S.C. 154(b) by 781 days.

(21) Appl. No.: 10/572,361

(22) PCT Filed: Sep. 15, 2004

(86) PCT No.: PCT/FR2004/050436
§ 371 (c)(1),
(2), (4) Date: Jan. 10, 2007

(87) PCT Pub. No.: WO2005/028513
PCT Pub. Date: Mar. 31, 2005

(65) Prior Publication Data
US 2007/0202102 A1    Aug. 30, 2007

(30) Foreign Application Priority Data
Sep. 16, 2003 (FR) ..................... 03 50543

(51) Int. Cl.
*C07K 16/06* (2006.01)
*C07K 16/24* (2006.01)
(52) U.S. Cl.
USPC ............... 424/130.1; 424/158.1; 530/387.1
(58) Field of Classification Search
None
See application file for complete search history.

(56) References Cited

U.S. PATENT DOCUMENTS

| 5,888,511 | A | * | 3/1999 | Skurkovich et al. | ....... 424/145.1 |
| 6,093,405 | A | * | 7/2000 | Zagury et al. | ............ 424/198.1 |
| 6,193,969 | B1 | * | 2/2001 | Landon | ...................... 424/158.1 |
| 6,333,032 | B1 | * | 12/2001 | Skurkovich et al. | ....... 424/130.1 |
| 7,285,269 | B2 | * | 10/2007 | Babcook et al. | ........... 424/142.1 |

FOREIGN PATENT DOCUMENTS

| FR | 2 838 444 | | 10/2003 |
| WO | WO 9729131 | * | 8/1997 |
| WO | WO 03/084979 A3 | | 10/2003 |

OTHER PUBLICATIONS

Bakhiet et al, J Interferon and Cytokine Research 9: 439-445, 1999.*
Harlow et al, In Antibodies a Laboratory Manual, 1988, Cold Spring harbor laboratory publication, Cold Spring Harbor, NY, pp. 56-59, 72-81, 288-289, 294-295 and pp. 312-318.*
Coligan et al, Curr Protoc Neurosci. Chapter 5:Unit 5.6, May 2001.*
Zagury, D. et al. Anti-IFNα immunization raises the IFNα-neutralizing capacity of serum—an adjuvant to antiretroviral tritherapy; Biomed & Pharmacother; vol. 53, 1999, pp. 90-92, XP-002277611.
Zagury, D. et al. "Toward a new generation of vaccines: The anti-cytokine therapeutic vaccines": Proceedings of the National Academy of Sciences of USA, Jul. 3, 2001, vol. 98, No. 14, XP-002186083.

* cited by examiner

*Primary Examiner* — Phuong Huynh
(74) *Attorney, Agent, or Firm* — Browdy and Neimark, PLLC

(57) ABSTRACT

The invention concerns a pharmaceutical composition comprising, as the active ingredient, human natural antibodies of the IgG isotype, that neutralize the activity of a human cytokine selected from VEGF, IFNα, IL-4, TNFα and TGFβ, the said neutralizing antibodies inhibiting at least 50% of the maximum biological activity induced by an amount ranging from 0.006 ng to 0.05 ng of the said cytokine in vitro.

20 Claims, No Drawings

HIGH-YIELD METHOD FOR THE PRODUCTION OF HUMAN ANTIBODIES BLOCKING THE BIOLOGICAL ACTIVITY OF A HUMAN CYTOKINE

FIELD OF THE INVENTION

The present invention relates to compositions comprising neutralizing antibodies which inhibit the biological activity of a cytokine, methods for their manufacturing, and their uses.

PRIOR ART

Cytokines are proteins produced by numerous cells, such as lymphocytes, monocytes, dendritic cells, mastocytes, fibroblasts, which exert autocrines, paracrine and endocrine effects on numerous tissues.

Cytokines influence cell survival, proliferation, differentiation and migration. Cytokines may be classified, in broad outline, according to their activity. Several are important in the induction of cell death, through a direct or indirect effect, via the generation of cytotoxic lymphocytes or NK cells (IFN-γ, TNF, IL-2, IL-15).

Other cytokines take part in allergy responses, such as IL-3, IL-4, IL-5, IL-9 and IL-13. Several cytokines are essential in the regulation of the antibody production (IL-4, IL-5, IL-6, IL-9, IL-10 and IL-13) whereas other cytokines exert a pro-inflammatory action (IL-1, TNFα, IFN-γ, chemokines). Still other cytokines possess anti-inflammatory properties (TGF-β, IL-4, IL-10). However, this categorisation does not reflect the complexity of the interactions between the cytokines and their cell targets, which are characterized by an important redundancy and pleiotropism, this without taking into account the agonist and antagonist effects. These features of the immune system and particularly of the cytokines explain why every interference with its mechanism, for example mediated by an antibody that blocks the cytokine, leads to important in vivo effects.

Until now, vaccine therapeutic strategies were mainly targeted towards the antigenic attacker, including a microorganism, a cell or an allergen, but were not focused on the fighting against cytokines deregulation. However, taken into account the key role of cytokines which are involved, for example, in the phenomena of escaping immune defences, or in the inflammatory phenomena, their inactivation in patients in view of acting on their activity or on their production is today a goal which is currently sought, all the more that the organism does not possess natural antagonists that are susceptible to counterbalance efficiently these cytokines. One knows, for example, anti-cytokine antibodies, but these antibodies are found with at a low title level, since B cells that produce them are resting. Further, these natural antibodies possess low affinity and do not neutralize the activity of the corresponding cytokine.

Notably, the phenomenon of cellular immune defences of the host mediated by the induction of their in situ paralysis consists of a strategy which is used numerous cancers and is required for their survival. Initially, immunosuppression remain localised at the tumor level, because the individual is still able to fight against the other aggressions, such as in infection. However, at a later stage, immunosuppression may extends, generalises, as shown by spreading of metastases and as shown by the high vulnerability of the cancer patients against infections, beyond the effects caused by chemotherapy or radiotherapy. As a summary, the said escape from the immune system control is caused by paralyses of the immune system (immunosuppression), which prevents it to function normally. The said immunosuppresion involves paralysing factors, including cytokines, which are produced by the cancer cells or by their environment. The local paralyses of the immune system cells, or immunosuppression, thus represents a major weapon of the cancer cells that allow them to escape to the immune system of the host.

The phenomenon of escapement from cell immune defences of the host, mediated by induction of their in situ paralyses is a strategy that is also used by HIV. Generalise immunosuppression that is observed in AIDS is notably characterized by an IFNα over production by the antigen presenting cells and particularly type 2 dendritic cells (DC2). The immunosuppressive activities of IFNα are due to its ability to induce the production of the IL-10 cytokine by regulatory T cells (formally named suppressive T cells).

A first strategy for inhibiting the biological activity of cytokines consists of injecting an immunogenic construct to a patient. For example, in order to induce recognizance of an antigen of interest, for example a cytokine, by B cells, various immunogenic construct were performed in the art. One embodiment of these immunogenic constructs consists of a covalent coupling between the antigen of interest and the carrier molecule, the said carried molecule bringing structures recognized by the helper T lymphocytes (also named "T-helper" cells), in combination with class II molecules of the major histocompatibility complex (MHC), which activate lymphocytes which thus produce various cytokines, including Il-2, which cytokines intern will activate B cell clones specific for the antigen of interest. The B cells specific for the antigen of interest, once activated, will multiply and produce antibodies specific for the antigen of interest, which is the goal which is sought. Generally, this kind of immunogenic construct consist of covalent chemical coupling products between the antigen of interest and the carrier molecule, which constructs, after a purification step and after a removing of the non-coupled products, consist of final product of a well defined chemical structure.

However, such kind of immunogenic constructions possess drawbacks, among which may be cited the large time period between the injection of the said constructs, and the appearance of an immune response directed against the targeted cytokine Additionally, it is sometimes impossible to efficiently vaccinate patients with anti-cytokines immunogenic constructs, when the said cytokines affect the intensity or the quality of the immune response. In fact, for example in the case of cancer or of AIDS, wherein a high magnitude immunosuppresion is observed, the administration of an immunogenic composition should, for being efficient, be performed at an early stage of the disease, particularly before that the immunosuppression be to much important.

There thus exists a need in the art for anti-cytokines antibodies which allow treating patients having an immune system break down. These antibodies act directly on the cytokines involved in immunosuppression, or also in the inflammatory process. Such a treatment by anti-cytokines antibodies allow to restore, at least temporarily, the immune response and may thus be used beforehand the administration of immunogenic compositions.

In the art, anti-cytokines antibodies are already known. For example, the patent application EP 1 285 930 as well as the corresponding U.S. Pat. No. 6,509,015 disclose human antibodies, specifically human recombinant antibodies, which bind specifically to TNFα, a cytokine produced by numerous cell types, and which is known for its role in auto-immune diseases, infections, or graft rejections.

It may be also cited the International Application No. WO 00/56772 which discloses human antibodies, preferably recombinants, which binds specifically to human IL-2, and neutralize its in vivo and in vitro activity.

It may finally be cited the US Patent Application No. 2003/0099647 which discloses agents binding to γ interferon and in particular the binding domains up to antibodies and to antigens that selectively bind to γ interferon and which may be used for preventing or treating inflammatory or auto-immune diseases, such as rheumatoid arthritis or lupus.

Taken into account the key role of the cytokines as reminded here above, there exist a long lasting need for novel antibody compositions having the ability to bind to cytokines of interest and to neutralize, at least partially, their biological activity. Importantly, such compositions should be non expensive, easy to prepare and being reproducibly synthesized.

SUMMARY OF THE INVENTION

The invention has for an object a high yield method for obtaining human antibodies that neutralize the biological activity of a human cytokine selected from VEGF, IFNα, IL-4, TNFα and TGFβ, comprising at least a step (a) of purifying:
  (i) the immunoglobulines contained in the serum of an individual, or
  (ii) the immunoglobulines produced by the B cells of an individual,
  the said individual having been previously immunised against the said cytokine, with a stable immunogenic product comprising protein immunogene heterocomplexes consisting of combinations between (i) molecules of antigenic proteins, selected from VEGF, IFNα, IL-4, TNFα and TGFβ and (ii) carrier protein molecules, in which less than 40% of the antigenic proteins (i) are linked to the protein carrier molecules (ii) through a covalent bound.

The present invention also provides novel compositions comprising anti-cytokine human natural antibodies as an active ingredient, which allow to overcome the problems encountered with the prior art immunogenic constructions disclosed above, and to provide an alternative to anti-cytokine antibody compositions already known.

Preferably, the neutralizing human natural antibodies that are selected as an active ingredient are polyclonal or monoclonal antibodies, and particularly, the polyclonal antibodies are selected from:
  (i) the whole antibody fraction purified from the serum of a human immunize against the said human cytokine;
  (ii) a purified fraction of monospecific polyclonal antibodies that neutralize the activity of the said cytokine;
  (iii) Fab or F(ab)'$_2$ fragments obtained from the said polyclonal antibodies (i) and (ii) above.

Preferably, the monoclonal antibodies are selected from:
  (i) antibodies produced by cells obtained after cell fusion between (a) B cells from a human individual immunised against the said human cytokine and (b) cells from an antibody producing cell line, such as myeloma cells;
  (ii) antibodies produced by cells transfected or transformed with a DNA encoding an immunoglobuline reproducing the antibodies induced by immunization and which are present in the serum of immunized patients, the said DNA being previously isolated from the DNA of a B cell from a human individual immunized against the said cytokine;
  (iii) Fab or F(ab)'$_2$ fragments prepared from the polyclonal antibodies (i) et (ii) above;
  (iv) ScFv fragments.

DETAILED DESCRIPTION OF THE INVENTION

It has been shown according to the invention that novel human antibodies having a high ability to neutralize the activity of a human cytokine, might be produced after immunization of a human individual against the said cytokine, without requiring complex steps of cell screening and of purification encountered in the prior art methods. There is a need to precise, for the sake of a better clarity, that an individual who is not immunized against a cytokine does not naturally possess antibodies that neutralize the activity of the said cytokine.

Such anti-cytokine antibodies are useful in various pathological contexts in which these cytokines are involved.

For example, it may be cited infections, autoimmune diseases, graft rejections, and generally all diseases related to an inflammatory reaction, like allergy. The antibodies according to the invention and the compositions comprising them are thus useful for fighting against this kind of disorder and additionally, are easy to obtain.

The invention pertains to a high yield method for obtaining human antibodies that neutralize the biological activity of a human cytokine selected from VEGF, IFNα; IL-4, TNFα and TGFβ, comprising at least a step (a) wherein it is purified:
  (i) the immunoglobulines contained the serum of an individual, or
  (ii) the immunoglobulines produced by the B cells of an individual,
the said individual having been previously immunised against the said cytokine, with an immunogenic product such as the one disclosed in the French Patent Application N° FR 02 11 455 filed on Sep. 16, 2002. Such a product consists of a stable immunogenic product comprising protein immunogenic heterocomplexes consisting of combination between (i) antigenic protein molecules selected from VEGF, IFNα, IL-4, TNFα and TGFβ and (ii) protein carrier molecules in which less than 40% of the antigenic proteins (i) are linked to the protein carrier molecules (ii) through a covalent bond.

VEGF (Vascular Endothelial Growth Factor), as well as IL-4 (Interleukine 4), IFNα (interferon α), TNFα (Tumor Necrosis Factor α) and TGFβ (Transforming Growth Factor β), will sometimes be termed herein under the same generic term "cytokine of interest" in the following of the specification.

Preferably, the said antibodies consist of "neutralizing" or "blocking" antibodies. A "neutralizing" antibody or a "blocking" antibody is defined, according to the invention, as an antibody the binding of which on the target cytokine blocks the biological activity of the said cytokine, which is the main goal which is sought according to the invention, when the said cytokine against which the said antibodies are directed possess a deleterious biological activity for the host organism.

According to the invention, the previous obtention of an immunisation of the individual against the cytokine of interest is detected, as it is illustrated in the examples, notably by a high serum level of the anti-cytokine antibodies in the immunised individuals. According to the invention, it has been observed that the human natural antibodies that neutralize the deleterious activity of a cytokine of interest were obtained in all the immunized individuals.

Without wishing to be bound by any particular theory, the inventors believe that the anti-cytokine human natural antibodies which are the subject matter of the present invention consist of high affinity antibodies. In other words, according to the inventors, the complexes formed between the said antibodies and the said cytokine against which these antibodies are directed, does not dissociate or hardly dissociate, which cause a drastic reduction in the circulating concentration of the free cytokine in an individual that has been administered with the antibodies defined in the present specification.

The immunisation of an individual against a cytokine may be performed by any mean known from the one skilled in the art. It may be preferred to administer the said individual with a cytokine the biological activity of which has been previously inactivated to 70%, to 90% or even to 95%, by a physical and/or chemical treatment, such as formulation, carboxamidation, maleimination, oxidation by oxygen bubbling, or by genetic recombination, or also by an adjuvant conditioning, the said treatment preserving sufficient immunogenic properties for generating antibodies that neutralize or block the said cytokine.

Most preferably, the human serum or the human B cells that produce the said antibodies originate from an individual who has been immunized with an immunogenic product such as disclosed in the French Patent Application No. FR 02 11 455 filed on Sep. 16, 2002. Such a product is a stable immunogenic product comprising protein immunogenic heterocomplexes consisting of combination between (i) antigenic protein molecules selected from VEGF, IFNα, IL-4, TNFα and TGFβ and (ii) protein carrier molecules in which less than 40% of the antigenic protein (i) are linked with protein carrier molecules (ii) by a covalent bond. By "antigenic protein" it is intended herein a cytokine, optionally chemically inactivated, or a cytokine fragment of at least ten amino acid residues in length, which is susceptible to be specifically recognized by the antigen receptors expressed by the B-lymphocytes from a host organism, either human or animal, particularly any mammal, which antigenic protein, once it is included in an immunogenic product, stimulates the production of antibodies recognizing the said cytokine.

The antigenic protein of interest may also consist of an homo-oligomer or homo-polymer of a native cytokine, or also of a homo-oligomer or a homo-polymer of a peptide fragment from a native cytokine. The antigenic protein of interest may also consist of an hetero-oligomer or of an hetero-polymer comprising in combination of several distinct peptide fragments that are initially included in the native cytokine.

By "protein carrier molecule", which is included in the immunogenic product, it is intended herein any protein or peptide of at least 15 aminoacid in length, whatever its aminoacid sequence, and which, when it is associated in a partially covalent manner to the molecules of antigen of interest for forming the protein heterocomplexes of the immunogenic product, allows the presentation of a high number of molecules of the said antigen of interest to be lymphocytes. Preferably, the protein carrier molecules are of KLH type (Keyhole Limpet Hemocyanin).

Preferably, the immunogenic product comprises additionally CpG oligodesoxynucleotides as an adjuvant, which allow to enhance the production of the antibodies that neutralize the activity of the cytokine of interest. The use of CpG oligonucleotides as adjuvant compounds in an immunogenic composition, in view of enhancing the immune response, is disclosed in the following documents: McCluskie M J et al. 2000; Gallichan W S, et al., 2001; and Eastcott J W et al., 2001.

As an example of a stable immunogenic product comprising efficient heterocomplexes, in view of inducing an immunisation, it may be cited a combination between the protein carrier molecule KLH (Keyhole limpet hemocyanin) and of human interferon-α molecules, such heterocomplexe product being hereafter termed interferon-α-KLH. The preferred immunogenic products are selected from the immunogenic products comprising the following heterocomplexes, in which the antigenic proteins (i), on one hand, and the protein carrier molecule (ii), on the other hand, are respectively:
  a)(i) VEGF and (ii) KLH;
  b)(i) interferon-α and (ii) KLH;
  c)(i) IL-4 and (ii) KLH;
  d)(i) TNFα and (ii) KLH;
  e)(i) TGFβ and (ii) KLH.

The percentage of protein carrier molecules and of antigenic proteins of interest that are linked together by covalent bounds, in a immunogenic product according to the invention, may be easily checked by the one skilled in the art.

For example, the determination of the percentage of the molecules of the antigen of interest that are bound to the protein carrier molecules through a covalent bound, in an immunogenic product according to the invention, may be assayed following the protocol that is disclosed in example 10.

Illustratively, the immunogenic product comprising heterocomplexes between the protein carrier molecule KLH (Keyhole limpet hemocyanin) and human α interferon molecules, only 3% of the interferon α molecules are covalently linked to the protein carrier molecule KLH.

The immunogenic product comprising immunogenic heterocomplexes as defined above may be prepared following the following steps:
  a) incubating the antigenic proteins (i) and the carrier molecule (ii) in a molar ratio (i):(ii) from 5:1 to 50:1, in the presence of a linking chemical agent;
  b) recovering the immunogenic product comprising the immunogenic heterocomplexes prepared in step a).

Preferably, the linking chemical agent consists of glutaraldehyde. Most preferably, the method above is further characterized in that step a) is following by a step for stabilizing the product comprising the immunogenic heterocomplexes, by formaldehyde, before performing step b) of recovering the said heterocomplexes.

Preferably, when glutaraldehyde is used as the linking chemical agent, it is present in the coupling reaction medium at a final concentration comprised between 0.002 M and 0.03M, preferably at a final concentration of 0.026 M.

The coupling reaction with glutaraldehyde is advantageously performed, during 20 minutes to 60 minutes, preferably 30 minutes at a temperature ranging from 20 to 25° C.

After the step of coupling, the excess glutaraldehyde is removed, for example by performing a dialysis with a dialyses membrane having a cut off threshold of 3 kDa. The dialyses step is advantageously performed at 4° C., in a buffer solution adjusted at pH 7.6.

In view of stabilizing the product comprising the protein heterocomplexes that is prepared at step a), the said product may be treated in solution by formaldehyde, for example by formaldehyde at a final concentration of 3 mM. The stabilization reaction has advantageously a duration comprised between 12 and 48 hours, preferably between 20 and 30 hours and is most preferably of 24 hours. The stabilisation reaction by formaldehyde is advantageously stopped by addition of glycine, preferably at a concentration of 0.1 M, during 1 hour and at a temperature ranging from 20 to 25° C.

The addition of CpG oligodesoxynucleotides is performed preferably after the step of removing of the excess glutaraldehyde.

The preparation of an immunogenic product comprising the immunogenic heterocomplexes as defined above is further illustrated in examples 1, 2, 3 and 4.

Although it is not illustrated in the examples, the preparation of heterocomplexes TGFβ-KLH, may be performed according to a protocol similar to the one disclosed in examples 1 to 4.

Typically, the neutralizing human natural antibodies according to the invention neutralize at least 50% of the maximum of the biological activity of the said cytokine of interest in vitro.

For example, it has been shown according to the invention, that the in vitro inhibition of at least 50% of the maximum biological activity of a cytokine of interest is usually obtained with an amount of neutralising human natural antibodies ranging from $10^{-3}$ μg to $10^{-2}$ μg.

The maximal biological activity of the cytokine interest in vitro is preferably induced by, respectively:
 (i) the minimal amount of VEGF causing maximal proliferation of the human umbilical vein endothelial cells;
 (ii) the minimal amount of IFNα causing maximal inhibition of the cell lyses from the MDBK cell line by the vesicular stomatitis virus (VSV);
 (iii) the minimal amount of IL-4 causing maximal proliferation of the IL-4-dependent TF-1 cell line;
 (iv) the minimal amount of TNFα causing maximal death of the TNFα-dependent L929 cell line;
 (v) the minimal amount of TGFβ causing maximal proliferation of the TGFβ-dependent NRK 49F cell line.

The biological activity assays for VEGF, human IFNα, IL-4 and TNFα may be performed notably according to the protocol disclosed respectively in the examples 5, 6, 7 and 8. The TGFβ biological activity assay may be performed in a manner similar to the one disclosed above, when using NRK 49F fibroblast cell line or according to a method known from the one skilled in the art.

Preferably, the said method comprises a step (b) of purifying the G isotype immunoglobulines from the immunoglobulines fraction obtains at the end of step (a).

The method according to the invention is particularly advantageous because it allows the obtention of a high level antibody response, as well as a high ratio of circulating B cells that produce antibodies that neutralize the activity of the cytokine of interest.

The isolated population of B-lymphocytes may be directly used, for example by fusing these B lymphocytes with myeloma cells in order to produce the anti-cytokine human natural antibodies, which allows to avoid complex purification processes.

The method according to the invention allows for example to avoid using methods for purifying B cells, such as panning, filtering through columns containing Nylon-coupled antibodies or also flow cytometry sorting (FACS®).

Obtaining B cells from an immunized individual is simple. A first method consists to isolate B lymphocytes from peripheral blood, by centrifugation in a density gradient consisting of a mixture of polysaccharide polymers (Ficoll®) and metrizamide, a ioded dense compound. At the interface, it is obtained a B lymphocyte population which is separated from the red blood cells and of most of the polynuclear cells.

Another method for obtaining B cells from an immunized individual consists of isolating B lymphocytes from tissues and particularly from lymphoid organs like spline, thymus, bone marrow, lymph nodes or lymphoid tissues related to the mucous membrane, such as palatin tonsils.

The method according to the invention may optionally comprise a further additional step for obtaining monospecific polyclonal antibodies that neutralize the biological activity of the said cytokine.

The method according to the invention may also comprise a further additional step of obtaining F(ab) or F(ab)′$_2$ fragments that neutralize the biological activity of the said cytokine.

The method according to the invention may also comprise the additional following steps:
 (i) using B cells obtained at the end of step (a) with cells from a myeloma, in view of obtaining an hybridoma line, and
 (ii) recovering the antibodies produced by the said hybridoma.

The whole steps will be disclosed hereafter in more details in the present specification, in relationship with pharmaceutical compositions.

The present invention also concerns a pharmaceutical composition characterized in that it comprises, as an active ingredient, human natural antibodies of IgG isotype, that neutralize the activity of a human cytokine selected from VEGF, IFNα, IL-4, TNFα and TGFβ, the said neutralizing antibodies inhibiting at least 50% of the maximal biological activity induced by the said cytokine in vitro.

As it flows from the present specification, the human antibodies that are contained in the said pharmaceutical composition as defined above are obtained from the serum or from B cells originating from an individual that has been previously immunized against the said cytokine of interest.

Typically, the human natural antibodies is according to the invention inhibit in vitro at least 50% of the biological activity that is induced by an amount ranging from 0.006 ng to 0.5 ng of the said cytokine of interest.

For example, it has been shown according to the invention that the in vitro inhibition of at least 50% of the maximal biological activity of the said cytokine of interest, for example when the said cytokine is used in the amounts specified above, is usually obtained with an amount of the said neutralizing anti-cytokine human natural antibodies ranging from $10^{-3}$ μg to $10^{-2}$ μg.

The immunisation of an individual against a cytokine may be performed by any method known from the one skilled in the art and in particular, in the case of INFα, by injection of an INFα previously inactivated by dimethylformamide, in the conditions disclosed in example 9.1. or by techniques identical to those which have been disclosed in relation to the method according to the invention.

Preferably, the said neutralizing human natural antibodies are obtained from the serum or from the B cells of an individual which has been immunized with a stable immunogenic product comprising protein immunogenic heterocomplexes consisting of combination between (i) protein antigenic molecules, respectively selected from VEGF, IFNα, IL-4, TNFα and TGFβ and (ii) protein carrier molecules in which less than 40% of the antigenic protein (i) are linked with protein carrier molecules (ii) through a covalent bond.

By "natural antibodies", it is intended herein exclusively antibodies such as they are naturally produced by the immunized individual, specifically against the cytokine of interest, the said natural antibodies being contained in the blood serum of the said individual, or these natural antibodies being produced, after immunisation, by the activated B cells of the said individual.

The definition of the heterocomplexes, their obtention, the determination of the percentage of covalent bound between the antigenic proteins and the carrier proteins, may be performed according to techniques identical to those which have been disclosed in relation to the method according to the invention.

Preferably, the maximal in vitro biological activity of the said cytokine is induced by, respectively:
(i) 0.5 ng VEGF;
(ii) 0.006 ng IFNα;
(iii) 0.5 ng IL-4.

The neutralizing anti-cytokine human natural antibodies according to the invention consist of polyclonal or monoclonal antibodies.

Preferably, the polyclonal antibodies are selected from:
(i) a whole antibody fraction purified from the serum of a human individual immunized against the said human cytokine;
(ii) a purified fraction of the monospecific polyclonal antibodies neutralizing the activity of the said cytokine;
(iii) Fab or F(ab)'$_2$ fragments prepared from the polyclonal antibodies (i) end (ii) above.

The obtention of the whole antibody fraction (i) purified from the serum of a human individual immunized against the said human cytokine comprises preferably the following steps:
a) injection of an immunogenic composition, preferably such as that disclosed above, to a human individual;
b) recovering the immune serum of the said human individual, containing the antibody that neutralize the activity of the administered antigen,
c) purifying the antibody fraction from the said immune serum.

Everyone of the steps of this method is disclosed in detail hereunder. The recovering of the immune serum is performed as known from the one skilled in the art, for example by separating the serum from a whole blood sample by centrifugation, the purification of an antibody fraction from the immune serum of an immunized patient, for example by affinity chromatography, ammonium sulphate precipitation, ion exchange chromatography, gel filtration, chromatography using a protein A/G column, affinity chromatography, or immuno-affinity chromatography.

An additional step of antibody purification, which is well suited to the present invention is disclosed in the European Patent Application EP 662 480. The said method allows to remove the anti-carrier molecule antibodies within an antibody mixture, and in particular, within an immune serum obtained at step (b).

A purified fraction of monospecific polyclonal antibodies (ii) that neutralize the activity of the cytokine of interest may be obtained by performing an affinity chromatography from a whole antibody fraction (i) purified from the immune serum of a human individual immunized against the said human cytokine, by binding an antigenic pattern on the cytokine of interest onto the column.

The purification of the F(ab)'$_2$ fragments from the polyclonal antibodies that are disclosed above, or from the immune serum or from the blood plasma, may be performed according to the method disclosed in the Patent Application No. US 2002/0164327, comprising a step of digesting blood plasma or serum by pepsin, and purification and separation steps until obtaining F(ab)'$_2$ fragments devoided of albumin, complete antibodies, and substantially devoided of pyrogenic substances.

The isolation of F(ab) and F(ab')$_2$ fractions allows to obtain specific advantages, such as the ability to bind to cytokines of interest without interacting with other effector molecules from the immune system.

The F(ab) fragments, may be obtained by a similar method, which consists of digesting the immune serum, the blood plasma or the polyclonal antibody purified fractions (i), (ii) and (iii) originating from an human individual immunized against the cytokine of interest, with papain.

Alternatively, the antibodies are monoclonal and selected from:
(i) antibodies produced by cells originating from the cell fusion between (a) B cells from a human individual immunised against the said human cytokine and (b) cells from an antibody-producing cell line, such as myeloma cells;
(ii) antibodies produced by cells transfected or transformed of a DNA encoding an immunoglobuline, the said DNA being previously isolated from the DNA originating from a B cells of a human individual immunised against the said human cytokine; according to a specific feature, the said immunoglobuline reproduces the antibodies induced by the immunization and which are present in the serum of the immunized patients.
(iii) the Fab or F(ab)'$_2$ fragments prepared from the polyclonal antibodies (i) and (ii) above;
(iv) ScFv fragments.

The monoclonal antibodies (i) may be obtained according to the following manner:

The first step consists of isolating the B-lymphocytes from a human individual against the human cytokine. A first method consists of isolating the B lymphocytes from the peripheral blood, by centrifugation in a density gradient consisting of a mixture of polysaccharide polymers (Ficoll®) and of metrizamide, a dense iodide compound. It is obtained at the interface a population of mononuclear cells which is separated from the red blood cells and of most of the polynuclear cells. The population of B lymphocytes may then be fused with myeloma cells or be subjected to an optional supplementary purification step, through the panning method, (i.e.) by binding to a substrate which is coated with antibodies allowing a specific adhesion of B-lymphocytes. The cells may also be filtered through columns containing Nylon-coupled antibodies that Coate steel wool, which allows elution of different cell populations, including B-lymphocytes.

These techniques may provide a preliminary step before sorting by FACS® which provides highly purified cell populations.

Another method consists of isolating B-lymphocytes from tissues and particularly from lymphoid organs, like spin, thymus, bone marrow, lymph nodes, or lymphoid tissues related to the mucous membrane, like palatine tonsils.

In case of a local immune response, the lymphocytes may be isolated at the site oft the immune reaction.

Thus, the isolated lymphocytes are then fused with mycelia cells, and the hybrid cells, or hybridomas, are then selected according to their affinity for the cytokine of interest; and the hybridoma that produce an antibody having the desired specificity are then identified and cloned by subculturing.

The antibodies produced by such hybridoma, which produce high affinity antibodies against the cytokine of interest consist of the monoclonal antibody fraction (i).

Particular type of B-lymphocyte may also be isolated by limit dilution culture, and selected according to the ability of the antibodies that are produced to bind to the cytokine of interest, before being fused with myeloma cells.

The DNA originating from a B-lymphocyte or from a hybridoma selected for its ability to produce high affinity antibody directed against a cytokine may then be isolated, and the DNA sequences encoding for the said antibody may be amplified according to conventional techniques in molecular biology. The thus amplified DNA is then inserted in cells, thus allowing the expression of the selected B lymphocyte antibodies. The thus produced antibodies consist of fraction (ii).

The F(ab) and F'(ab')₂ fragments (iii) may be isolated according to an enzyme method identical to the one disclosed above for the polyclonal antibodies.

The scFv fragments (iv) or "single chain variable fragment" may be synthesized according to the following method:

DNA sequences encoding for the variable domain of the heavy chain and for the variable domain of a light chain are selected from the DNA originating from a B lymphocyte, or from a hybridoma as disclosed above. This selection may be performed by selecting specific primers, according to conventional techniques in molecular biology. Such DNA sequences are then cloned in an expression vector, with a sequence encoding a synthetic peptide, the whole of which is to bind the variable domains.

The said expression vector is then inserted in a host cell. Examples of expression vectors and of host cells which are suitable for expressing antibodies and antibody fragments are provided hereafter.

It may be cited, as an example of host cells, well suited for the synthesis of an scFv fragment, the L-Form cells from *Proteus mirabilis* as disclosed by Rippmann et al. (1998).

The synthesis of scFv fragments allows to obtain specific advantages due to the small size of the said fragments, which allow them to easily diffuse in the tissues.

It is also possible to synthesis the F(ab) and F(ab)'₂ fragments according to the method disclosed above for the sc Fv fragments.

Although, this does not consist of a preferred embodiment of the invention, the neutralizing anti-cytokine human natural antibodies according to the invention may consist in recombinant antibodies. In this embodiment, DNA fragments originating from a B lymphocyte or from a hybridoma selected according to the method disclosed above, are subjected to modifications. Particularly, the DNA encoding for the variable domains of the said antibody, and in particular for the variable domains of the heavy chain (VH) and of the light chain (VL) may be randomly mutated, in view of enhancing the affinity of these fragments for the cytokine of interest. The variable domains may also be mutated in the CDR3 region according to method analogous to the somatic mutation which is responsive of the maturation and of the affinity of the antibodies during the natural immune response. The maturation and the affinity in vitro may be performed by amplifying the sequences encoding the VH and VH domains by polymerisation chain reaction (PCR) and using primers complementary to the CDR3 regions, harbouring random mutations, in view of having the VL and VH domains amplified and mutated. These domains are then newly screamed for their ability to bind to the cytokine of interest, and the domains that present the most important affinity for the cytokine are selected. The DNA encoding the VL and VH domains is then reinserted, either within the sequences encoding the constant region of the antibody to which they originate, or within the sequences encoding the constant regions of any other immunoglobulines.

The thus obtained DNA sequences, which encode for complete recombining antibodies or for scFv fragment or for VH or VL domains, are then introduced in expression vectors and in host cells, examples of which will be provided hereafter.

Other antibodies that are encompassed by the definition of the invention may be obtained through a screening using an expression phage library, which may be prepared using cDNA encoding for VL and VH domains, these cDNA being prepared from MRNA originating from human lymphocytes.

The methods from preparing these libraries are known per se. As an example of such expression phage library, it may be cited the "Recombinant Phage Antibody System" which is marketed by Pharmacia. Embodiments of obtaining and of screening expression phage libraries are provided in the U.S. Pat. No. 5,223,409 and in the International Application No. PCT WO 92/20791.

In a preferred embodiment of the invention, the anti-cytokine human monoclonal antibodies such as disclosed above are used for selecting the VH and VL domains having properties of binding to similar cytokines. This selection is performed for instance by the epitope imprinting method, or by the methods disclosed in the International Application No. PCT WO 93/06213. The antibody libraries used according to this method will preferably be scFv libraries.

Once the VH and VL domains are selected, they are then mixed and then screamed according to their ability to bind to a selected cytokine. The DNA sequence encoding the VH and VL domain pairs may then be randomly mutated, in view of enhancing the affinity towards the selected cytokine. The VH and VL domain pairs may also be mutated in the CDR3 region according to a method analogous to the somatic mutation responsive of the maturation of the affinity of the antibodies during the natural immune response.

The maturation of the in vitro affinity may be performed according to the method disclosed hereunder, related to the DNA of a B lymphocyte selected for its ability to bind to a cytokine. The aminoacid sequences of the selected VH and VL domains may then be compared to the corresponding aminoacid sequences of the germlines cells, because of the occurrence of sequence differences, which are due for example to the type of library that has been used during the first screening. In this case, it may useful to perform reverse mutations in the corresponding DNA sequences, in view of finding the initial aminoacid sequence.

Such reverse mutation may be performed according to conventional methods in molecular biology, which allow to introduce specific mutations, such as site-directed mutagenises.

After such a selection, the nucleic acids encoding the antibodies of interest may be cloned in expression vectors according to conventional techniques. The nucleic acids may also be subjected to an additional step consisting of generating other antibodies encompassed by the definition according to the invention. For example, it may consist of adding sequences encoding for additional immunoglobuline domains, such as additional constant regions.

The DNA sequence encoding recombinant antibodies or antibody fractions, and particularly the VH and VL domains may be introduced in a suitable cell line, such as non-antibody producing myeloma cells used for preparing hybridomas, in view of producing recombinant antibodies selected for their ability to bind to the cytokine of interest.

This DNA sequences may also be cloned in a recombinant expression vector that is introduced in a mammal host cell, such as disclosed hereunder.

The preferred host cells are CHO cells (Chinese Hamster Ovary), the myeloma cells NSO, the COS cells and the SP2 cells. When the expression vectors comprising the sequences encoding these antibodies, the recombinant antibodies, and the antibody fragments, are introduced in host cells, these cells are cultured during period of times of a length sufficient for these antibodies or these fragments be produced in the host cells, or even better, released in the culture medium wherein are located the host cells. The antibodies are then recovered by standard protein purification techniques.

Pharmaceutical Compositions and Administration

The compositions according to the invention are preferably pharmaceutical compositions comprising neutralizing anti-cytokine human natural antibodies as disclosed above, including antibody fragments. Particularly, a composition according to the invention comprises additionally at least one physiologically acceptable excipient.

The term "physiologically acceptable excipient" encompasses for example solvents, dispersion media, anti-bacterial agents, anti-fungal agents or also dilution agents allowing to reach isotony. Among these excipients according to the invention, it may be cited water, phosphate buffer, dextrose, glycerol, ethanol and their combinations. It is often preferred to add to the composition, also isotonic agents such as sugars, polyalcohols, like mannitol or sorbitol or also sodium chloride. The composition may additionally comprise auxiliary substances, like emulsifying agents, preservatives or buffers that will enhance efficiency or used duration of the compositions according to the invention may be presented in various forms, and may be for example liquid or under the form of solid or semi-solid injection dosage that are aimed to be infused before injection. Other forms may be conceivable like for example suspensions, dispersions, tablets, powders, liposomes or also suppositories. Preferred compositions are under the form of solutions for injection, similar to those which exist for human passive vaccination with antibodies other than those disclosed in the present application. The preferred administration mode of these compositions is the parenteral route, (for example subcutaneous or intramuscular route) or intravenous.

The compositions of the invention, should be sterile and also stable in the conventional manufacturing and stocking conditions. The compositions according to the invention may be solutions, microemulsions, dispersions, liposomes and other structures. The preparation of sterile injectable compositions may be performed by incorporating the active ingredient, i.e. the antibody or the antibody fragment, in the appropriate amount of solvent and of other excipients such as those disclosed above, and by then performing a sterilization by filtration.

It may be eventually conceive that the composition according to the invention comprises a first type of antibody, such as those disclosed above, which neutralize the activity of cytokine and a second type of antibodies directed for example against the known receptors or targets of the said cytokines.

Taking into account the pleiotropic role of the cytokines, and in particular the role in the inflammatory reaction and in the response to infections, it may be advantageous to combine a composition according to the invention with an additional active ingredient, involved in the fight against inflammation, infection, asthma, or also graft rejections, or auto-immune diseases.

Examples of therapeutic agents for fighting against inflammation, which may be used in combination with the antibodies according to the invention are:

The budenosid, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants compounds, thromboxane inhibitors, Il-10 receptors antagonists, anti-IL-1β monoclonal antibodies, anti-IL-6 monoclonal antibodies, elastase inhibitors, soluble form type 1 complement receptors, and others.

Examples of therapeutics agents for fighting against infection, which may be used in combination with the antibodies according to the invention are antibiotics, iron chelators, apoliprotein 1 reconstituted with lipids, hydroxamic acids, (synthetics antibacterian agents).

Pharmaceutical compositions according to the invention may include an "efficient pharmaceutical amount" of an antibody or of an antibody fragment according to the invention. By "efficient pharmaceutical amount", it is intended herein an efficient amount, at dosages and for a sufficient duration allowing to lead to the therapeutic result which is sought. This amount varies depending on various factors such as pathological state, sex, weight and age of the patient to be treated, and also of the ability of the said antibody to induce an effect in the patient. Such an amount should lead to side effects or toxic effects lower in comparison to the benefits that are brought by the treatment with the composition according to the invention.

The dosage may be adapted in view of obtaining an optimal response. For example, the pharmaceutical composition may be administered through a single dosage or through several dosages administered at regular time periods.

Uses According to the Invention

Taken into account the ability of the antibodies contained in the compositions according to the invention to bind to cytokines, the antibodies according to the invention may be used for detecting cytokines in vitro, using conventional techniques such as affinity chromatography, "ELISA" type techniques (enzyme-linked immunosorbent assays) or also "RIA" (radioimmunoassay).

The invention thus concerns a method for detecting a cytokine in a sample, comprising a step of bringing into contact the said composition according to the invention with the samples to be analysed and the step of detecting the complexes formed between the antibody and a cytokine.

In order to facilitate the detection of a complex, the said antibody may be labelled by a detectable substance, for example enzymes like horseradish peroxydase, alkaline phosphatase, β-galactosidase or also acetylcholine esterase, prosthetics groups like streptavidine/biotins, and avidin/biotins, fluorescent molecules like ombelliferone, fluorescein, rhodamin, phycoerythrin, or radioactives molecules like $^{125}$I; $^{131}$I, $^{35}$S, or $^{3}$H.

The invention also concerns a method for detecting the presence and the amount of a cytokine in a sample of an unknown constitution, by titration through competitive inhibition. The said method makes use of antibodies according to the invention and of a reference cytokine, which is labelled.

According to this titration method, the biological sample, the labelled reference cytokine and the antibody according to the invention are combined and the amount of the reference cytokine which is bound to the antibody is then determined. The amount of the cytokine within the sample is inversely correlated with the amount of the reference cytokine bound to the antibody according to the invention.

The invention also pertains to:
- the use of the anti-VEGF antibodies for manufacturing a pharmaceutical composition for the treatment of cancer.
- The use of the anti-IFNα antibodies for manufacturing a pharmaceutical composition for the treatment of an immunosuppression state;
- The use of the anti-IL-4 antibodies for manufacturing a pharmaceutical composition for the treatment of allergy.
- The use of the anti-TNFα antibodies for manufacturing a pharmaceutical composition for the treatment of an immunosuppression state.
- The use of the anti-TGFβ antibodies for manufacturing a pharmaceutical composition for the treatment of the infection by a retrovirus or for the treatment of a cancer selected from the group consisting of colon cancer, breast cancer and prostate cancer.

Methods of Treatment According to the Invention

Preferably, the composition according to the invention may be used in the framework of an anti-cytokine vaccination, as a preliminary step to a conventional vaccination, the goal of which is neutralize or block the immunotoxic effect of the stroma, and to allow the normal rizing of an immune reaction adapted against an antigenic attacker.

The invention has thus also for an object a method of treatment comprising at least the following steps:
(i) administering a composition according to the invention to a patient;
(ii) administering to the said patient an immunogenic composition, containing an antigen or a combination of antigens inducing an immune response which is sought, against the said antigen or against the said antigen combination.

The said two-steps method allows to re-establish the immune response of a patient, before the said patient be vaccinated against the agent which is responsive of the immune break down.

EXAMPLE 1

KLH-Human VEGF Heterocomplex

This heterocomplex is directed to induce mainly within the vaccinated patient, the production of antibodies that neutralize the human VEGF.

0.58 mg of KLH protein are dissolved in 0.5 ml of phosphate buffer 10 mM pH 8.5. To this solution, it is added 1 mg human VEGF dissolved in 1 ml of the same buffer.

The thus obtained mixture is then treated by glutaraldehyde at the final concentration of 0.026M during 30 minutes at laboratory temperature.

The excess glutaraldehyde is then removed by three successive dialysis steps of two hours duration each, which are performed with a dialysis membrane with a cut off threshold of 3 kDa, at 4° C., against 200 ml of phosphate buffer pH 7.6 10 mM.

The mixture is then treated by formaldehyde at the final concentration of 33 mM during 24 hours. Then the reaction is stopped by addition of glycine 0.1 M final concentration during 1 hour at ambient temperature.

The mixture is then dialysed in the same conditions that the dialysis steps disclosed previously.

EXAMPLE 2

Preparation of a KLH-IFNα Heterocomplex

This conjugate is aimed to induce mainly in the vaccinated individual the production of antibodies that neutralize human INFα.

0.625 mg of KLH protein are dissolved in 0.6 ml borate buffer 10 mM pH 8.8 150 mM NaCl. To this solution are added 1 mg of human TNFα protein dissolved in 1 ml of the same buffer.

The protein mixture thus obtained is then treated by glutaraldehyde at the final concentration 0.026 M during 30 minutes at ambient temperature.

The excess glutaraldehyde is then removed by three successive dialysis steps of two hours duration each, which are performed with a dialysis membrane with a cut off threshold of 3 kDa, at 4° C., against 200 ml of phosphate buffer pH 7.6 10 mM.

The mixture is then treated by formaldehyde at the final concentration of 33 mM during 48 hours. Then the reaction is stopped by addition of glycine 0.1 M final concentration during 1 hour at ambient temperature. The mixture is then dialysed in the same conditions that the dialyse steps disclosed previously.

EXAMPLE 3

Preparation of a KLH-human IL-4 Heterocomplex

This heterocomplex is aimed at inducing mainly in the vaccinated individual the production of antibodies that neutralize human IL-4.

1 mg of KLH protein is dissolved in 1 ml phosphate buffer 10 mM pH 8.5. To this solution are added 1 mg of murine IL-4 protein dissolved in 1 ml of the same buffer.

The protein mixture thus obtained is treated by glutaraldehyde at the final concentration of 0.026 M during 30 minutes at ambient temperature.

The excess glutaraldehyde is then removed by 3 successive steps of dialysis of 2 hours duration each, with a dialysis membrane having a cut off threshold of 3 kDa, at 4° C. against 200 ml phosphate buffer pH 7.6 10 mM.

The mixture is then treated by formaldehyde at the final concentration of 33 mM during 24 hours. Then the reaction is stopped by addition of glycine 0.1 M final during 1 hour at ambient temperature. The mixture is then dialysed in the same condition as the dialysis steps performed previously.

EXAMPLE 4

Preparation of a KLH-Murine TNFα Heterocomplex

This conjugate is aimed at inducing mainly in the vaccinated individual the production of antibodies that neutralise murine TNFα.

0.625 mg of KLH protein are dissolved in 0.6 ml borate buffer 10 mM pH 8.8 150 mM NaCl. To this solution are added 1 mg of human INFα protein dissolved in 1 ml of the same buffer.

The protein mixture thus obtained is treated by glutaraldehyde at the final concentration of 0.026 M during 45 minutes at ambient temperature.

The excess glutaraldehyde is then removed by three successive steps of dialysis of 4 hours duration each which are performed with a dialysis membrane having a cut off threshold of 3 kDa, at 4° C., against 200 ml of phosphate buffer pH 7.6 10 mM 150 mM NaCl.

The mixture is then treated by formaldehyde at the final concentration of 33 mM during 48 hours. Then the reaction is stopped by addition of glycine 0.1 M final during one hour at ambient temperature.

The mixture is then dialysed in the same conditions than the dialysis steps previously performed.

EXAMPLE 5

VEGF Biological Activity Assay

Human umbilical vein endothelial cells (HUVECs) are cultured in flat bottomed wells of a microculture plate at a cell density of 3000 cells by wells. Various dilutions of antibodies are then added on the cultured endothelial cells. The cell cultivation is pursued at 37° C. in wet atmosphere at 5% $CO_2$ during 3 days. 18 hours before the end of the incubation, 0.5 µCi of tritiated thymidine are added in each well.

The neutralizing antibodies prevent murine VEGF to induce endothelial cells proliferation, whereas non-neutralizing antibodies allows cell proliferation.

EXAMPLE 6

Human IFNα Biological Activity Assay

MDBK cells are cultivated in round bottomed wells of a microculture plate at density of 350 000 cells by well. Various dilutions of IFNα are then added on the MDBK cells.

After 20 hours of cell cultures performed at 37° C. in a wet atmosphere in 5% $CO_2$, the dilutions are removed, the cells are washed, then 100 µl containing 100 $DL_{50}$ (lethal dose 50%) of VSV are added. 18 hours after addition of the virus, the lysis effect of the viruses is measured.

The neutralizing antibodies allow VSV to lyse cells, whereas non-neutralizing antibodies prevent this lysis.

EXAMPLE 7

Human IL-4 Biological Activity Assay

This assay makes use of TF-1 cells, a human cell line the growth of which depends on human IL-4 (Kitamura, T. et al., 1989. J. Cell. Physiol 140:323-34). TF-1 cells are cultured in round bottomed wells of a microculture plate at the cell density of 10000 cells by well. Various dilutions are then added to the TF-1 cells. The cell culture is pursued at 37° C. in wet atmosphere at 5% $CO_2$ during 3 days. 4 hours before the end of the incubation, 0.5 µCi of tritiated thymidine are added in each well.

The neutralizing antibodies prevent human IL-4 to induce proliferation of TF-1 cells, whereas non neutralizing antibodies allow proliferation of these cells.

EXAMPLE 8

TNFα Biological Activity Assay

L929 cells are cultured in flat bottomed wells of a microculture plate. Various dilutions of TNFα are then added on the cells. The cell culture is pursued at 35° C. in wet atmosphere at 5% $CO_2$ during 3 days. 4 hours before the end of the incubation, 5 mg/ml MTT are added (MTT is available near Company SIGMA Chemical, St-Louis, Mo.).

The neutralizing antibodies prevent TNFα to induce the death of the endothelial cells, conversely, to non-neutralizing antibodies.

EXAMPLE 9

Comparison Between the Biological Activity of Antibodies According to the Invention and Commercially Available Neutralizing Antibodies

EXAMPLE 9.1

Production of an Anti-Interferon α Polyclonal Antibody in Human

A group of voluntary individuals was immunized after administration by intramuscular route of human α interferon that have been inactivated by a chemical treatment by dimethylformamide. Each voluntary individual was subjected to an injection of 710 µg of inactivated IFNα, at Day 0, D7, D14, D21 and D42.

The production curve of the anti-interferon α antibodies was determined in function of the time. At the production pic (when the level of the anti-IFNα IgG isotype immunoglobuline thus generated was of about 9.5 µg by ml), 20 ml of blood were sampled in each of the vaccinated individual and a pool of sera was prepared. The anti-α interferon activity of the pool of sera was determined by ELISA and the antibody titer was found to be 128 000 (inverse of the dilution giving a D0 of 0.300).

The IgG fraction was isolated from a portion of the pool of sera by ammonium sulphate precipitation (($NH_4)_2SO_4$ at 35% saturation. After dialysis, the solution containing IgG antibodies that neutralize the IFNα activity thus obtained with a 80% yield presented an ELISA result of 512 000.

The neutralizing potency (amount of antibodies allowing to inhibit 50% of the biological activity of 1 UI of human α interferon) of the whole anti-α interferon serum and of the IgG originating therefrom was 0.004 µg and 0.001 µg, respectively.

TABLE 1

|  | Ab of example 9.1 | Ab rabbit polyclonal (1) | Ab sheep polyclonal (2) | Ab mouse monoclonal (3) |
| --- | --- | --- | --- | --- |
| Human IFNα (1 UI) | 0.04 µg | 0.01 µg | 0.0005 µg | 0.8 µg |

The table 1 establishes a comparison between the neutralizing potency of the anti-α interferon polyclonal antibody produced as disclosed above with the neutralizing potency of commercially available antibodies. The neutralizing potency obtained with the antibody produced as disclosed above is about 200 times higher as regards the titer obtained with a mouse monoclonal antibody.

(1) Rabbit polyclonal antibody directed against IFNα, available near company PBL Biomedical Pharmaceutical under reference No. 31 100-1.

(2) Sheep polyclonal antibody directed against IFNα, available near company PBL Biomedical Pharmaceutical under Ser. No. 31130-1.

(3) Mouse monoclonal antibody directed against IFNα, available near company PBL Biomedical Pharmaceutical under Ser. No. 21105-1.

EXAMPLE 9.2

Production of an Anti-IL-4 Polyclonal Antibody in Human Individuals

Volunteer human subject was immunised by intramuscular administration of a KLH-human IL-4 conjugate.

This individual subject has undergone an injection of 120 µg of human IL-4 that was chemically inactivated by dimethylformamide at D 0, D21 and D 60.

The production curve of the anti-IL antibodies was determined in function of time. At the pic of antibody synthesis, when the level of anti-IL4 IgG isotype immunoglobuline thus generated was of about 12 µg/ml) a blood sampling was performed and the anti-IL4 serum was collected. The ELISA measure of the serum activity has given an antibody titer of 512,000 (inverse of the serum dilution giving an ELISA measure value of 0.300. After separation of the IgG fraction containing the anti-IL4 antibodies, the said fraction has been digested by pepsine and the F(ab')$_2$ antibody fragment was collected with a yield of 60% The determination of ELISA activity as given a measure value of 310,000. The neutralizing potency (amount of antibodies allowing to inhibits 50% of the activity of 0.5 ng of interleukine-4) of the whole anti-IL-4 serum was established to be 0.02 μg and, for F(ab')$_2$ fraction, to be 0.1 μg.

TABLE 2

|  | Ab of example 9.2 | Goat polyclonal Ab (1) | Rabbit polyclonal Ab (2) | Mouse monoclonal Ab(3) |
|---|---|---|---|---|
| Human IL-4 (0.5 ng) | 0.02 μg | 0.08 μg | 0.01 μg | 1 μg |

Table 2 establishes the comparison between the neutralizing potency of the anti-IL-4 polyclonal antibody produced as disclosed above with the neutralizing potency of commercially available antibodies. The antibody titer obtained with the antibody produced as disclosed above is about 50 times higher than the antibody titer obtained with a mouse monoclonal antibody.

(1) Goat polyclonal antibody against IL-4 available near company R&D under the reference N° AF-204-NA.

(2) Rabbit polyclonal antibody directed against IL-4 available near company Peprotech under reference N°500-P24.

(3) Mice polyclonal antibody directed against IL-4 available near company R&D under reference N°MAB204.

EXAMPLE 9.3

Production of a Anti-Murine VEGF Polyclonal Antibody in Mice

A method similar to the one disclosed for examples 7.1 and 7.2 has been used. A group of 20 mice was immunized by administration of a KLH-murine VEGF heterocomplex. Each mouse has been subjected to an injection of 20 μg of VEGF which was chemically activated by dimethylformamide at D 0, D7, D14, D21 and D42.

By referring to the production curve of the anti-VEGF antibodies, a blood sampling was performed in all mice at the pic of response and a pool of anti-VEGF sera was prepared.

The IgG fraction was isolated by precipitation with $(NH_4)_2SO_4$ at 35% saturation. The ELISA activity was determined and was equal to 256 000 and the neutralizing activity of the IgG fraction (amount of antibodies allowing to inhibit 50% of the activity of 0.5 ng of murine VEGF) was 0.012 μg.

TABLE 3

|  | Antibody of example 9.3 | Goat polyclonal antibody (1) | Rabbit polyclonal antibody (2) | Mouse monoclonal antibody (3) |
|---|---|---|---|---|
| VEGF (0.5 ng) | 0.012 μg | 0.001 μg | 0.007 μg | 0.003 μg |

Table 3 establishes a comparison between the neutralizing potency of the anti-murine VEGF polyclonal antibody produced as disclosed above, with the neutralizing potency of the commercially available anti-VEGF antibodies.

(1) Goat polyclonal antibody directed against VEGF, available near Company R&D under reference AF-293-NA.

(2) Rabbit polyclonal antibody directed against the VEGF available near company Peprotech under Ser.N° 500-P10.

(3) Mouse polyclonal antibody directed against VEGF available near the Company R&D under reference N°MAB293.

EXAMPLE 9.4

Production of a Recombinant Monoclonal Antibody Directed Against Human IFNα

Material:

Human peripheral blood mononuclear cells (PBMC) originate from a subject immunized with human IFNα which was chemically activated.

The Epstein Barr virus (EBV) was prepared from a culture supernatant of the B95-8 cell line and used at a concentration of $10^5$ TD$_{50}$/ml.

Culture:

The human PBMCs were purified on a Ficoll density gradient and then infected with the virus. The cells transformed by EBV are then cultivated in round bottomed 96 well culture plates at the cell concentration of $5\times10^3$-$10^4$/ml with RPMI 1640 (culture medium) (GIBCO BRL, Life Technologies) added with 20% foetal calf serum SVF (Gibco BRL, Life Technologies). The culture medium is changed every four days time period. After 4 to 6 weeks of cell culture, the cells are transferred into 24 well plates and then finally transferred in six wells culture plate. The culture supernatant is then analysed by ELISA technique.

Selection of the Anti-IFNα Monoclonal Antibody Producing Clones

Clones producing anti-IFNα antibodies are selected and put in mass cell culture. A monoclonal antibody was purified from a culture supernatant, by adsorption on a Sepharose Protein A column. The thus produced monoclonal antibody was purified by adsorption. The solution containing the purified anti-IFNα monoclonal antibody has a content in monoclonal antibodies of 1 mg/ml and its neutralizing activity (ability of inhibiting 50% of the activity of 1 UI of IFNα (or ND50 is equal to 0.7 μg.

These clones produce antibodies that represent a high yield cell material for the production of a human monoclonal antibody directed against human IFNα, having high affinity, through using of the phage display technology well known from the from the one skilled in the art and disclosed in the present application.

TABLE 4

|  | Antibody of example 9.4 | Rabbit polyclonal antibody (1) | Sheep polyclonal antibody (2) | Mouse polyclonal antibody (3) |
|---|---|---|---|---|
| Human IFNα (1 UI) | 0.7 μg | 0.01 μg | 0.0005 μg | 0.8 μg |

Table 4 establishes a comparison between the neutralizing potency of the IFNα monoclonal antibody produced as disclosed above with the neutralizing potency of commercially available antibodies.

The antibody titer obtained with the antibody produced as disclosed above is about 50 times higher than the antibody titer obtained with a mouse monoclonal antibody.

(1) Rabbit polyclonal antibody directed against IFNα, available near company PBL Biomedical Pharmaceutical under reference N° 31100-1.

(2) Sheep polyclonal antibody directed against IFNα, available near société PBL Biomedical Pharmaceutical under reference N° 31130-1.

(3) Mouse polyclonal antibody directed against IFNα, available near société PBL Biomedical Pharmaceutical under Ser. N° 21105-1.

EXAMPLE 10

Determination of the Percentage of Cytokine Bound to the Protein Carrier Molecule (KLH) by Double Sandwich ELISA Technique The percentage of cytokine which is linked to the protein carrier molecule (KLH) was determined by a double sandwich ELISA technique, using a capture antibody directed specifically against the carrier protein.

100 µl of horse polyclonal antibodies directed against KLH (1 mg/ml) diluted in a phosphate buffer 10 mM pH 7.3 NaCl 150 mM (PBS) are fixed in wells of a microtitration plate (High binding, Costar) during 2 hours at 37° C. After three washings in PBS/0.1% Tween 20 (PBST), the wells are saturated with PBS containing 2% PBS. After 1 h 30 duration of saturation, the wells are washed three times with PBST, then two-fold dilutions of heterocomplex (10, 5, 2.5, 1.25, 0.625, 0.312 and 0.156 µg/ml), duplicate, are added in the wells (100 µl/well). After two hours incubation, the wells are washed three times with PBST. The tween, the dissociating agent, which is present in the washing buffer, allows the removing of all the molecules which are not covalently bound to KLH, KLH being specifically fixed on the capture antibody. Then, the two heterocomplex dilutions are treated according to two ways:
 a) the first serial is incubated with an antibody directed against KLH,
 b) the second serial is incubated with an antibody directed against the cytokine.

After 1 h 30 incubation time period, at 37° C., the wells are washed as previously described and then incubated with a secondary antibody coupled to peroxydase, said second antibody being directed against the initial animal species of the first antibody. After a 1 h 30 incubation time period at 37° C., the wells are again washed. Then, the addition of the peroxydase substrate, namely, O-phenylenediamine, (OPD), allows to reveal the presence of the KLH bound to the capture antibody and of the cytokines which are covalently linked to KLH.

The amount of KLH bound to the capture antibody, then the amount of the molecules of the cytokine linked covalently to KLH are calculated using calibration curves performed using ELISA technique.

The percentage of covalently bound cytokine which is covalently bound to KLH is then determined.

BIBLIOGRAPHIC REFERENCES

Eastcoft J W, Holmberg C J, Dewhirst F E, Esch T R, Smith D J, Taubman M A. (2001) Oligonucleotide containing CpG motifs enhances immune response to mucosally or systemically administered tetanus toxoid. Vaccine. 2001 Feb. 8; 19(13-14):1636-42.

Gallichan W S, Woolstencroft R N, Guarasci T, McCluskie M J, Davis H L, Rosenthal K L. (2001) Intranasal immunization with CpG oligodeoxynucleotides as an adjuvant dramatically increases IgA and protection against herpes simplex virus-2 in the genital tract. J Immunol. 2001 Mar. 1; 166(5):3451-7.

Kitamura T, Tange T, Terasawa T, Chiba S, Kuwaki T, Miyagawa K, Piao Y F, Miyazono K, Urabe A, Takaku F. (1989) Establishment and characterization of a unique human cell line that proliferates dependently on GM-CSF, IL-3, or erythropoietin. J Cell Physiol August; 140(2):323-34.

McCluskie M J, Weeratna R D, Davis H L (2000) Intranasal immunization of mice with CpG DNA induces strong systemic and mucosal responses that are influenced by other mucosal adjuvants and antigen distribution. Mol Med. October; 6(10):867-77.

Rippmann J F, Klein M, Hoischen C, Brocks B, Rettig W J, Gumpert J, Pfizenmaier K, Mattes R, Moosmayer D. (1998) Procaryotic expression of single-chain variable-fragment (scFv) antibodies: secretion in L-form cells of *Proteus mirabilis* leads to active product and overcomes the limitations of periplasmic expression in *Escherichia coli*. Appl Environ Microbiol. 1998 December; 64(12):4862-9.

The invention claimed is:

1. A pharmaceutical composition comprising, as the active ingredient, polyclonal human natural antibodies of the IgG isotype that neutralize the activity of human TNFα wherein:
 (i) said antibodies inhibit at least 50% of the maximal biological activity that is induced by TNFα in vitro, as assessed by the L929 cell assay;
 (ii) said antibodies originate from the serum of an individual immunized with a stable immunogenic product comprising protein immunogenic heterocomplexes consisting of combinations of (i) molecules of human TNFα and (ii) Keyhole Limpet Hemocyanin (KLH) protein carrier molecules in which less than 40% of the human TNFα molecules (i) are linked with the KLH protein carrier molecules (ii) through a covalent bond, wherein the stable immunogenic product is produced by a method comprising the steps of:
  (a) incubating in a coupling reaction the TNFα molecules (i) and the KLH molecules (ii) in a molar ratio (i):(ii) of from 5:1 to 50:1 in the presence of glutaraldehyde at a concentration between 0.002M and 0.03 M;
  (b) removing excess glutaraldehyde after the coupling reaction;
  (c) treating the product obtained in step (b) in a stabilization reaction with formaldehyde;
  (d) stopping the stabilization reaction with formaldehyde by the addition of glycine; and
  (e) recovering the immunogenic product comprising the immunogenic heterocomplexes prepared in step (d); and
 (iii) said antibodies are selected from the group consisting of:
  (A) a whole fraction of antibodies purified from the serum of a human individual immunized against said human TNFα;
  (B) a purified fraction of monospecific polyclonal antibodies neutralizing the activity of the said human TNFα; and
  (C) Fab or F(ab)'$_2$ fragments prepared from the polyclonal antibodies (A) and (B) above.

2. A method for treating a patient undergoing immunosuppression, comprising administering the pharmaceutical composition according to claim 1 to the patient.

3. A high yield method for obtaining polyclonal human natural antibodies of the IgG isotype that neutralize the activity of human TNFα, as assessed by the L929 cell assay, comprising the steps of:
 (A) administering to a human individual an immunogenic composition which comprises a stable immunogenic product comprising protein immunogenic heterocomplexes consisting of combination between (i) molecules of human TNFα and (ii) Keyhole Limpet Hemocyanin (KLH) protein carrier molecules, in which less than 40% of the human TNFα molecules (i) are linked with the KLH protein carrier molecules (ii) through a covalent bond, wherein the stable immunogenic product is produced by a method comprising the steps of:

(a) incubating in a coupling reaction the TNFα molecules (i) and the KLH molecules (ii) in a molar ratio (i):(ii) of from 5:1 to 50:1 in the presence of glutaraldehyde at a concentration between 0.002M and 0.03 M;

(b) removing excess glutaraldehyde after the coupling reaction;

(c) treating the product obtained in step (b) in a stabilization reaction with formaldehyde;

(d) stopping the stabilization reaction with formaldehyde by the addition of glycine; and (e) recovering the immunogenic product comprising the immunogenic heterocomplexes prepared in step (d); and (B) recovering the immune serum of the human individual, containing the polyclonal human natural antibodies; and (C) purifying the antibody fraction from the immune serum.

4. The method according to claim 3, further comprising a step of purifying the IgG isotype antibodies from the antibodies fractions obtained at the end of the step of purifying the antibody fraction from the immune serum.

5. The method according to claim 3, further comprising an additional step of obtaining monospecific polyclonal antibodies neutralizing the biological activity of human TNFα.

6. The method according to claim 3, further comprising an additional step of obtaining the F(ab) or F(ab)′$_2$ fragments neutralizing the biological activity of human TNFα.

7. The pharmaceutical composition of claim 1, wherein, in step (a) of the method for producing the stable immunogenic product, the incubation in the coupling reaction is in a range of 20 to 60 minutes at a temperature in a range of 20° C. to 25° C.

8. The pharmaceutical composition of claim 1, wherein, in step (a) of the method for producing the stable immunogenic product, the incubation in the coupling reaction is in a range of 45 minutes at a temperature in a range of 20° C. to 25° C.

9. The pharmaceutical composition of claim 1, wherein, in step (b) of the method for producing the stable immunogenic product, excess glutaraldehyde is removed by dialysis with a dialysis membrane having a cut off threshold of 3 kDa.

10. The pharmaceutical composition of claim 1, wherein, in step (c) of the method for producing the stable immunogenic product, the product obtained in step (b) is treated with formaldehyde in a range of 12 to 48 hours.

11. The pharmaceutical composition of claim 1, wherein, in step (c) of the method for producing the stable immunogenic product, the formaldehyde is in a final concentration of 33 mM.

12. The pharmaceutical composition of claim 1, wherein, in step (c) of the method for producing the stable immunogenic product, the treatment with formaldehyde in the stabilization reaction is carried out for 48 hours.

13. The pharmaceutical composition of claim 1, wherein, in step (d) of the method for producing the stable immunogenic product, the stabilization reaction with formaldehyde is stopped by the addition of 0.1 M glycine at a temperature in a range of 20° C. to 25° C.

14. The method of claim 3, wherein, in step (a) of the method for producing the stable immunogenic product, the incubation in the coupling reaction is in a range of 20 to 60 minutes at a temperature in a range of 20° C. to 25° C.

15. The method of claim 3, wherein, in step (a) of the method for producing the stable immunogenic product, the incubation in the coupling reaction is in a range of 45 minutes at a temperature in a range of 20° C. to 25° C.

16. The method of claim 3, wherein, in step (b) of the method for producing the stable immunogenic product, excess glutaraldehyde is removed by dialysis with a dialysis membrane having a cut off threshold of 3 kDa.

17. The method of claim 3, wherein, in step (c) of the method for producing the stable immunogenic product, the product obtained in step (b) is treated with formaldehyde in a range of 12 to 48 hours.

18. The method of claim 3, wherein, in step (c) of the method for producing the stable immunogenic product, the formaldehyde is in a final concentration of 33 mM.

19. The method of claim 18, wherein, in step (c) of the method for producing the stable immunogenic product, the treatment with formaldehyde in the stabilization reaction is carried out for 48 hours.

20. The method of claim 3, wherein, in step (d) of the method for producing the stable immunogenic product, the stabilization reaction with formaldehyde is stopped by the addition of 0.1 M glycine at a temperature in a range of 20° C. to 25° C.

* * * * *

UNITED STATES PATENT AND TRADEMARK OFFICE
CERTIFICATE OF CORRECTION

PATENT NO. : 8,679,483 B2  Page 1 of 1
APPLICATION NO. : 10/572361
DATED : March 25, 2014
INVENTOR(S) : Bizzini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this
Twenty-ninth Day of September, 2015

Michelle K. Lee
*Director of the United States Patent and Trademark Office*